United States Patent [19]

Alvarez

[11] 4,261,984
[45] Apr. 14, 1981

[54] 17β-THIOCARBOXYLIC ACID ESTERS OF 3-OXO-4-HALO-16β-METHYLANDROST-4-ENES

[75] Inventor: Francisco S. Alvarez, Sunnyvale, Calif.

[73] Assignee: Syntex (U.S.A.) Inc., Palo Alto, Calif.

[21] Appl. No.: 70,579

[22] Filed: Aug. 29, 1979

Related U.S. Application Data

[63] Continuation-in-part of Ser. No. 893,390, Apr. 5, 1978, Pat. No. 4,198,403.

[51] Int. Cl.³ .............................. C07J 1/00; C07J 3/00; A61K 31/56
[52] U.S. Cl. ................................ 424/238; 260/397.1; 260/397.45; 260/239.55 C; 260/239.55 R; 260/239.55 D
[58] Field of Search ...... 260/397.1, 397.45, 239.55 D, 260/239.55 C; 424/238

[56] References Cited

U.S. PATENT DOCUMENTS

| 2,897,199 | 7/1959 | Ringold et al. | 260/397.45 |
| 3,489,748 | 1/1970 | Els et al. | 260/239.55 |
| 3,707,537 | 12/1972 | Kierstead | 260/239.55 C |
| 4,188,385 | 2/1980 | Edwards | 260/397.1 |

*Primary Examiner*—Elbert L. Roberts
*Attorney, Agent, or Firm*—Tom M. Moran; Alan M. Krubiner

[57] ABSTRACT

Certain 3-oxoandrost-4-ene and 3-oxoandrosta-1,4-diene 17β-thiocarboxylic acid esters substituted at the 4-position with a fluoro or chloro, optionally substituted at the 6-position with fluoro or chloro and at 16β with methyl are useful as anti-inflammatory steroids. These compounds are optionally substituted at the 9α position with fluoro, chloro or bromo; substituted at the 11 with a keto, a beta-hydroxy or a beta-chloro (the latter only when there is a 9α-chloro); when there is a 17α-hydroxy (or an ester).

12 Claims, No Drawings

17β-THIOCARBOXYLIC ACID ESTERS OF 3-OXO-4-HALO-16β-METHYLANDROST-4-ENES

This is a continuation-in-part application of U.S. patent application Ser. No. 893,390, filed Apr. 5, 1978 now U.S. Pat. No. 4,198,403.

BACKGROUND OF THE INVENTION

1. Field of the Invention

This invention relates to novel of alkyl, benzyl or phenyl 3-oxoandrost-4-ene 17β-thiocarboxylates and the corresponding androsta-1,4-dienes set forth as Formula (I) hereafter. More specifically it relates to anti-inflammatory 17β-hydroxy-16β-methyl compounds which are substituted at the 4 position with fluoro, chloro or bromo and are optionally substituted at the 6α-position with fluoro or chloro. The invention further relates to pharmaceutical anti-inflammatory compositions comprising a compound of the invention in combination with a pharmaceutically acceptable excipient.

2. Prior Art

Certain 3-oxoandrost-4-ene 17β-carboxylic acids which are substituted at the 9 position with chlorine or fluorine and at the 11 position with keto or hydroxy or chloro group are known. See for example U.S. Pat. No. 3,828,080. It is known that 3-oxoandrost-4-ene 17β-carboxylic acids may be substituted at both the 9α and 6α positions with fluoro. See for example U.S. Pat. Nos. 3,636,010 and 4,093,721.

It is also known from U.S. Pat. No. 3,989,686 to Phillipps et al of Glaxo that steroids of Formula (II)

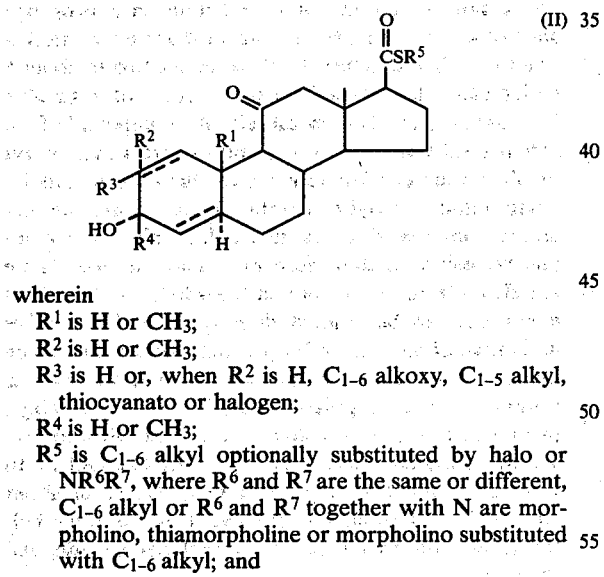

wherein
- $R^1$ is H or $CH_3$;
- $R^2$ is H or $CH_3$;
- $R^3$ is H or, when $R^2$ is H, $C_{1-6}$ alkoxy, $C_{1-5}$ alkyl, thiocyanato or halogen;
- $R^4$ is H or $CH_3$;
- $R^5$ is $C_{1-6}$ alkyl optionally substituted by halo or $NR^6R^7$, where $R^6$ and $R^7$ are the same or different, $C_{1-6}$ alkyl or $R^6$ and $R^7$ together with N are morpholino, thiamorpholine or morpholino substituted with $C_{1-6}$ alkyl; and
- the dotted lines in the "A" ring represent an optional double bond at these positions. These compounds are useful as anesthetics.

Methyl 3β-acetoxyallothiol-cholonate and methyl 3β-acetoxy-etiothiolchol-5-enate are also known compounds. See, e.g., Jerger et al, Helv. Chem. Acta. 29, 684–92 (1946).

A heretofore unknown series of 3-oxoandrost-4-ene 17β-thiocarboxylates being substituted at the 4 position with fluoro, chloro or bromo and optionally substituted at the 6 position with fluoro or chloro has been discovered and is disclosed herein. The compounds exhibit good anti-inflammatory activity and few adverse side effects.

SUMMARY OF THE INVENTION

One aspect of this invention is a compound chosen from those represented by Formula (I) wherein

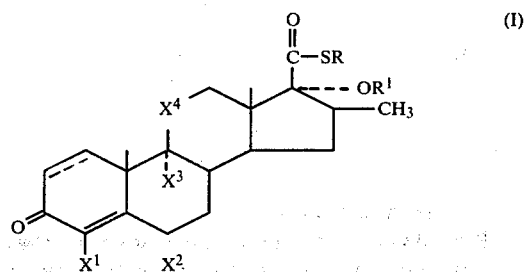

Z is sulfur;
$X^1$ is fluoro or chloro;
$X^2$ is fluoro, chloro or hydrogen;
$X^3$ is fluoro, chloro, bromo or hydrogen;
$X^4$ is =C=O or $$=C\begin{matrix}OH\\H\end{matrix}$$

or may also be

when is $X^3$ chloro;

R is alkyl of 1 through 6 carbon atoms or phenyl or benzyl optionally substituted with one substituent chosen from the group consisting of alkyl of 1 through 4 carbon atoms and halo;

$R^1$ is hydrogen or alkanoyl of 2 through six carbon atoms; and the solid and broken lines between C-1 and C-2 represent a single or double bond.

Another aspect of this invention is an anti-inflammatory pharmaceutical composition which comprises at least one suitable pharmaceutical excipient in combination with a therapeutically effective amount of a compound chosen from those represented by Formula (I), as defined above, wherein each of the substituents are as defined. Particularly valuable compounds for this composition are set forth hereinafter.

Still another aspect of this invention is a process for treating an inflamed condition in a mammal which comprises administering a therapeutically effective amount of a compound chosen from those represented by Formula (I), above, wherein substituents are as defined above, to said mammal.

Still another aspect of this invention is a process for preparing a compound of this invention and is discussed hereafter.

DETAILED DESCRIPTION AND PREFERRED EMBODIMENTS

Compounds

In its broadest aspect, this invention is a compound chosen from those represented by Formula (I) wherein
$X^1$ is fluoro or chloro;

$X^2$ is fluoro, chloro or hydrogen;
$X^3$ is fluoro, chloro, bromo or hydrogen;
$X^4$ is =C=O or

or is

when $X^3$ is chloro;

R is alkyl of 1 through 6 carbon atoms or phenyl or benzyl optionally substituted with 1 substituent chosen from the group consisting of alkyl of 1 through 4 carbon atoms, alkoxy of 1 through 4 carbon atoms and halo;

$R^1$ is hydrogen or alkanoyl of 2 through 6 carbon atoms; and the solid and broken lines between C-1 and C-2 represent a double or single bond.

One subgroup of the broad aspect of the invention comprises those compounds represented by Formula (I) wherein $X^1$ is fluoro or chloro; $X^2$ is fluoro or hydrogen; $X^3$ is fluoro, chloro or hydrogen; $X^4$ is

or may also be

when $X^3$ is chloro; R is alkyl of 1-6 carbon atoms; and $R^1$ is alkanoyl of 2-6 carbon atoms. A subdivision of this subgroup includes those compounds of Formula (I) wherein $X^1$ is fluoro, $X^2$ is hydrogen or fluoro, $X^3$ is hydrogen or fluoro, $X^4$ is

and there is a double bond between C-1 and C-2. Of the compounds of this subdivision, the preferred compounds are represented by Formula (I) wherein $X^1$, $X^2$ and $X^3$ are all fluoro, R is methyl and $OR^1$ is acetate, propionate or butyrate.

In defining the compounds of this invention the term "alkyl" includes both straight chain and branched alkyl groups, thus alkyl of 1-6 carbon atoms includes methyl, ethyl, n-propyl, isopropyl, n-butyl, isobutyl, t-butyl, pentyl, isoamyl, n-hexyl and the like. The phenyl and benzyl substituents may be substituted on the phenyl ring at the 2, 3 or 4 positions with one substituent such as alkoxy of 1-4 carbons (e.g. methoxy, ethoxy, n-propoxy, t-butoxy and the like), alkyl of 1-4 carbons (e.g., methyl, ethyl, isopropyl, n-propyl, t-butyl, n-butyl, etc.), or a halo such as fluoro, chloro, bromo or iodo. Preferably the substitution is at the 2 or 4 positions.

The term "alkanoyl" refers to a radical of the formula

wherein $R^4$ is alkyl of 1-5 carbon atoms and includes e.g. acetyl, propionyl, butyryl, valeryl, caproyl, and the like.

In naming the compounds of this invention the substituents present on the androstane ring shall be included numerically and the compounds shall be alkyl (or phenyl or benzyl) 17β-thiocarboxylates. For example, if in Formula (I), above, $X^1$ and $X^2$ are fluoro, $X^3$ and $X^4$ are chloro, R is methyl and $R^1$ is acetoxy the name is methyl 3-oxo-4,6α-difluoro-9α,11β-dichloro-16β-methyl-17α-acetoxyandrosta-1,4-diene 17β-thiocarboxylate. If, on the other hand, R is hydrogen but $X^1$, $X^2$, $X^3$, $X^4$ and $R^1$ are the same, the compound is named 3-oxo-4,6α-difluoro-9α,11β-dichloro-16β-methyl-17α-acetoxyandrosta-1,4-diene 17β-thiocarboxylic acid.

Compound Preparation

Compounds of the invention are readily prepared by converting an appropriate androst-4-ene 17β-carboxylic acid (or a reactive derivative thereof) to the corresponding 17β-thiocarboxylate of this invention. This conversion is carried out by reacting an appropriate androst-4-ene 17β-carboxylic acid (or a reactive derivative thereof) with a molar excess (about 1.05 to about 5 molar equivalents based on the steroid) of a suitable basic salt, e.g. an alkali metal salt, of a compound of the formula RSH where R is the appropriate alkyl, benzyl or phenyl moiety. Representative alkali metal salts include sodium methyl mercaptan, sodium ethyl mercaptan, sodium benzyl mercaptan, sodium phenyl mercaptan, potassium methyl mercaptan, and the like. These are also referred to as sodium thioalkylates. The alkali metal salt can be reacted directly with the reactive derivative of the 17β-carboxylic acid, or the salt can be formed in situ by mixing an alkali metal hydride, such as sodium hydride or potassium hydride, with an alkyl, phenyl or benzyl mercaptan. The thioesterification reaction readily takes place at temperature of about 10° to 100° C. (preferably at ambient temperature of about 20°-25° C.) in a suitable inert solvent such as dimethylformamide, diethylformamide, dimethylacetamide, and the like.

The reactive derivative of the 17β-carboxylic acid may be an acid chloride, but is preferably a mixed anhydride, such as the dialkyl or diphenyl phosphate ester prepared by reacting a dialkyl (1-4 carbons) or diphenyl chlorophosphate (e.g. diethyl chlorophosphate or diphenyl chlorophosphate) with the appropriate 17β-carboxylic acid in an inert solvent such as tetrahydrofuran (THF) under an inert atmosphere (nitrogen) at temperatures of about 10°-50° C., preferably about 20°-25° C.

Certain 16β-methyl starting compounds are prepared according to Reaction Sequence 1.

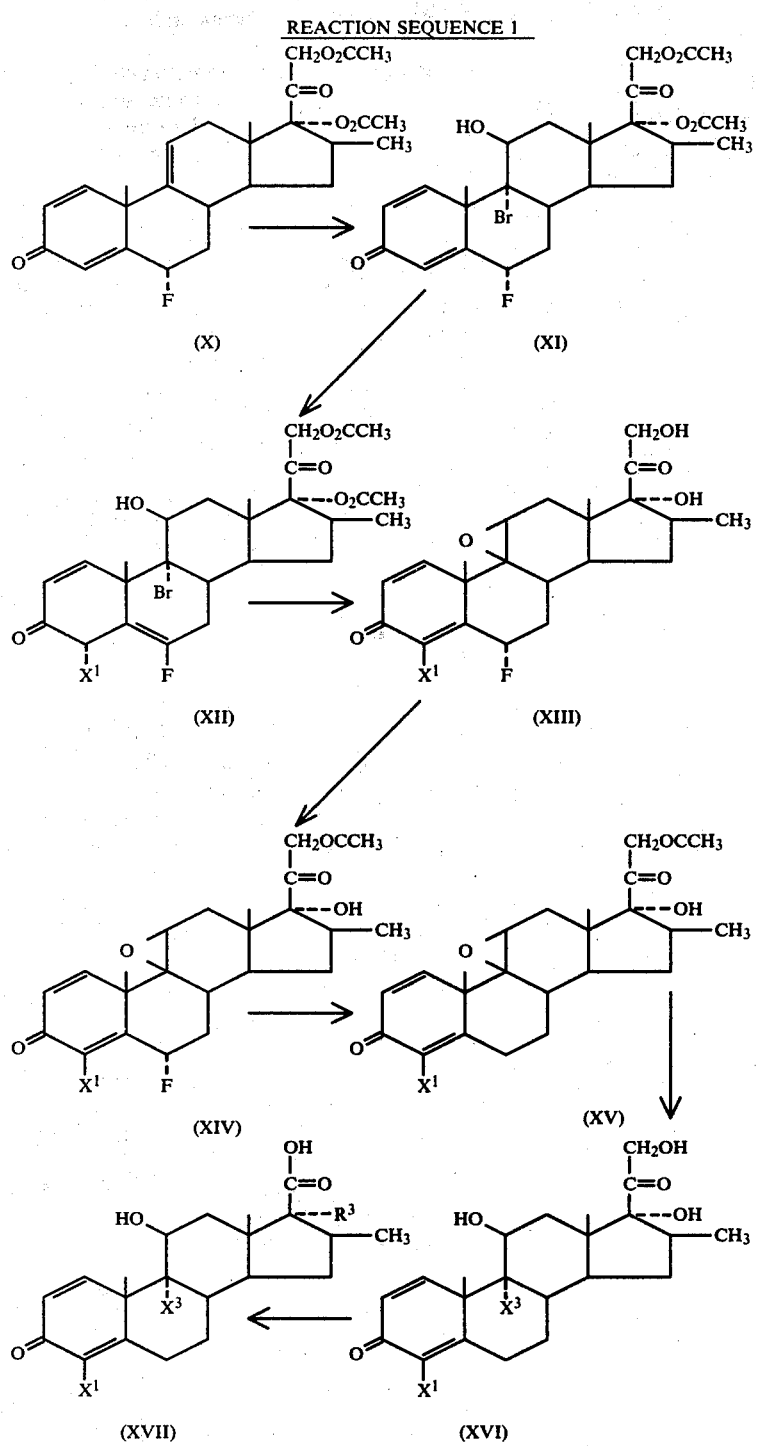

REACTION SEQUENCE 1

(X) (XI) (XII) (XIII) (XIV) (XV) (XVI) (XVII)

The starting compound in this sequence is shown as Formula (X). This is a known compound, e.g. see British Pat. No. 1,403,962. The starting material is converted into the 9,11-bromohydrin of Formula (XXI) by treating with dibromohydantoin according to methods well known in the art. This compound is readily halogenated to the 4-fluoro or 4-chloro compound of Formula (XXII) by treatment with trialkyl orthoformate and then with perchlorofluoride or N-chlorosuccinimide.

The first step of the halogenation process is performed by reacting a compound of Formula (XI) to form an intermediate 3-methoxy-Δ³- or 3-ethoxy-Δ³-11β-orthoester compound. This is carried out by reacting, for example, a large molar excess of trimethyl orthoformate in methanol or triethyl orthoformate in ethanol in the presence of a catalytic amount (i.e. less than 5% by weight) of a suitable acid catalyst such as fuming sulfuric acid at reflux temperature or less. About 50°–55° C. is preferred. Generally the molar ratio of the orthoformate to steroid is about 10:1 to about 30:1. Once the reaction is complete a base is added to neutralize the acid and the resulting product is recovered and purified using methods well known in the art such as recrystallization, chromatography, etc.

This compound is then halogenated using perchloryl fluoride ($ClO_3F$) or trifluoromethoxy fluoride ($CF_3OF$) as a fluorinating agent, a source of positive chlorine such as N-chlorosuccinimide, dichlorohydantoin, etc. as a chlorinating agent to form the 3-keto-4α-fluoro (chloro) steroid represented by Formula (XII).

In the case of $ClO_3F$, which is a gas, an approximately equimolar amount, i.e. about 1 to 1.1 moles $ClO_3F$ per mole of the 3-methoxy intermediate is metered into a mixture of the compound in a solution which is a major amount of acetone, preferably 90% by volume, and a minor amount water, preferably about 10%, over a period of about 1-3 hours at about −75° to 20° C., preferably starting at about −75° C. and allowing the reaction mixture to slowly warm to ambient temperatures. Dichlorohydantoin or N-chlorosuccinimide are reacted using a solvent such as acetone and water or tetrahydrofuran and water to dissolve the reactants and adding the halogenating solution to the compound in a similar solvent at about −50° C. to about 50° C.

The resulting compound of formula (XII), in turn, is recovered and reacted with potassium fluoride in DMSO then with a suitable base such as an alkali metal carbonate, e.g. potassium carbonate, in a suitable oxygenated hydrocarbon solvent such as an alkanol, e.g. methanol, in an inert atmosphere, to rearrange the pregna-1,5-diene and form the desired 4-fluoro(4-chloro)-3-oxopregna-1,4-diene represented by Formula (XIII). The potassium carbonate is sufficient for basis hydrolysis of the 17α- and 21-esters.

This, in turn, is converted to the 21-acetate of Formula (XIV) by reaction with acetic anhydride in pyridine.

The 21-acetate, in turn, is treated with zinc metal dust and cupric acetate (e.g. 3%) and acetic acid in anhydrous methanol and methylene chloride at ambient temperatures to give a 6-desfluoro compound of Formula (XV).

By treatment with basic methanol in an inert atmosphere, this compound is hydrolyzed to the 17α,21-dihydroxy compound (not shown), which in turn is then be converted to the corresponding fluorohydrin, chlorohydrin or bromohydrin by methods known in the art such as using hydrofluoric acid, hydrochloric acid or hydrobromic acid, respectively to give a compound of Formula (XVI) wherein $X^1$ is fluoro or chloro and $X^3$ is fluoro, chloro or bromo. This then is converted to the 17β-carboxylic acid of Formula (XVII) by treatment with periodic acid ($HIO_6$) in aqueous methanol at temperatures of 10°–50° C., e.g. about 25° C.

Another procedure for preparing compounds of this invention is set forth in Reaction Sequence 2, below.

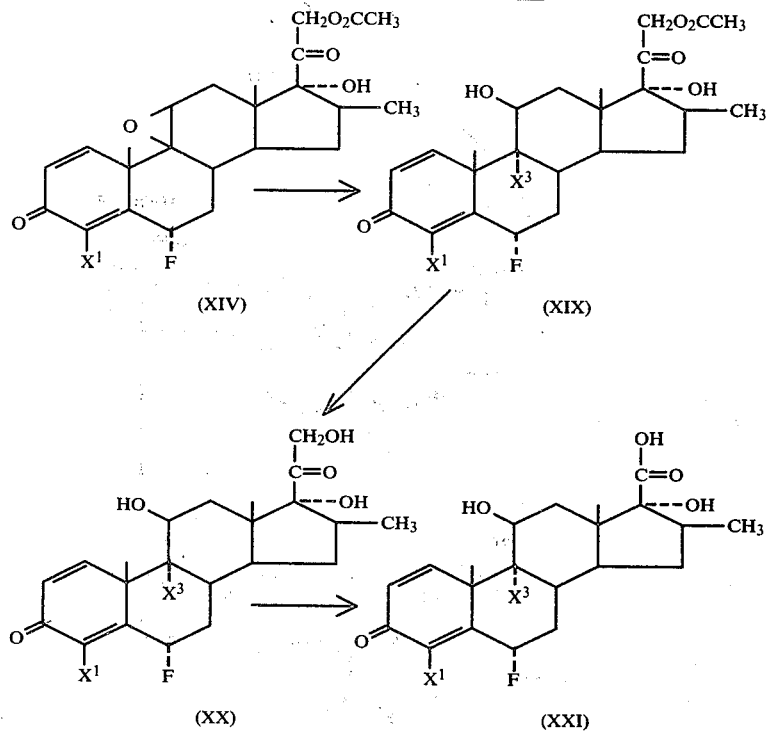

REACTION SEQUENCE 2

In this process the intermediate compound represented by Formula (XXIV), prepared as discussed above for Reaction Sequence 1, is reacted, for example, with HF in tetrahydrofuran and chloroform at very low temperatures (−70° C.) or with a HF/urea complex according to the process of U.S. Pat. No. 3,211,758 to Tarkoey. This forms a compound represented by Formula (XXIX) (where $X^3$ is fluoro) which is elaborated to other compounds of Formula (XXI) by methods discussed hereinbefore.

Another process for preparing 9α-chloro compounds of this invention is set forth in Reaction Sequence 3, below.

REACTION SEQUENCE 3

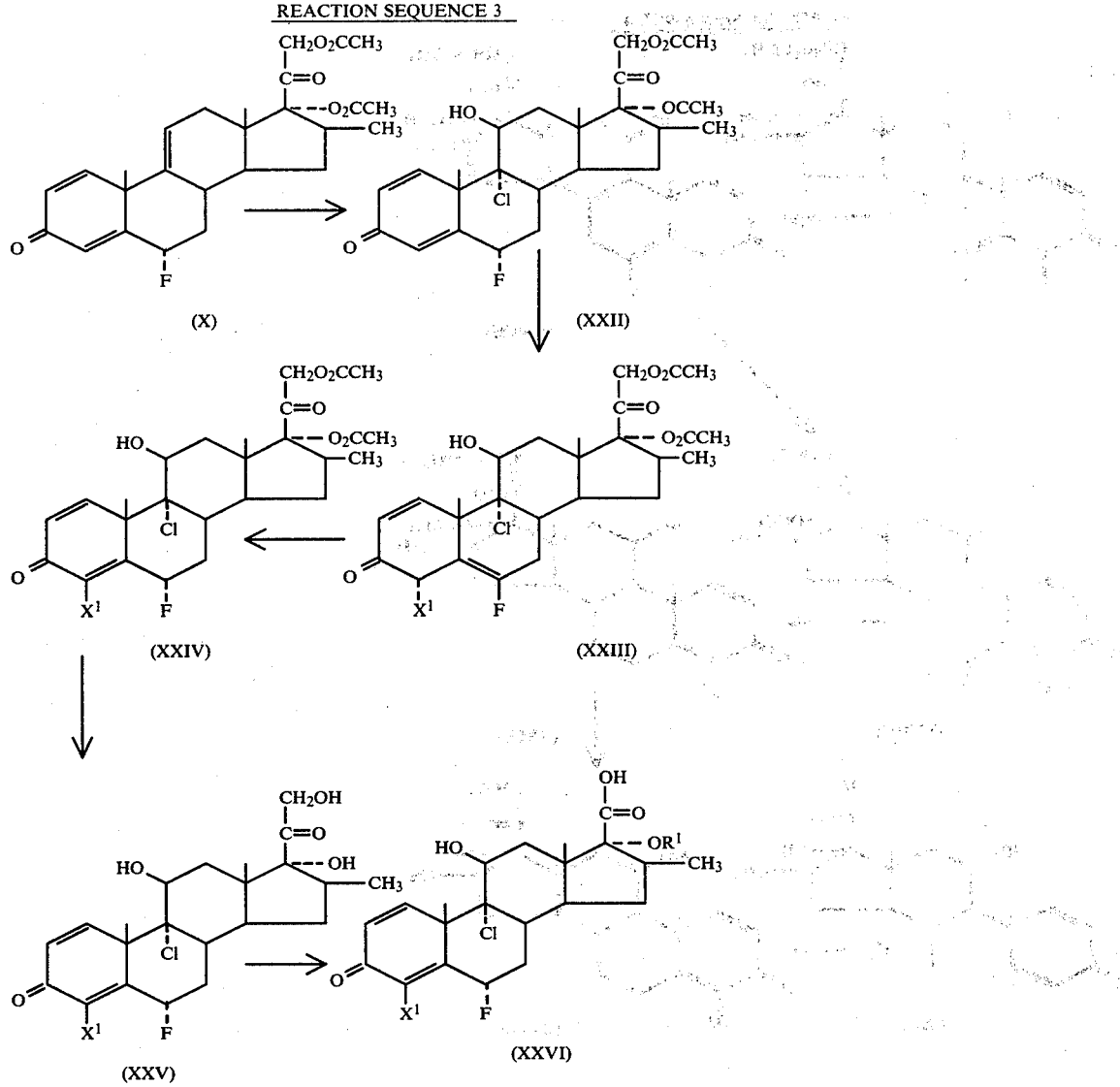

In the first step of Reaction Sequence 3, the 1,4,9(11)-triene is reacted with Halane (1,3-dichloro-5,5-dimethylhydantoin) to form the 9,11-chlorohydrin of Formula (XXII). This, in turn, is fluorinated or chlorinated at the 4-position using procedures set forth hereinbefore to give a compound represented by Formula (XXIV) which is hydrolyzed to the 17α,21-dihydroxy compound using perchloric acid in aqueous methanol at temperatures of about 20° C. to the boiling point of the mixture. The compound represented by Formula (XXIV) is to other compounds represented by Formula (XXVI) wherein $X^1$ and $R^1$ are defined above.

Methods of preparing 9α-unsubstituted compounds of this invention are set forth in Reaction Sequence 4, below.

REACTION SEQUENCE 4

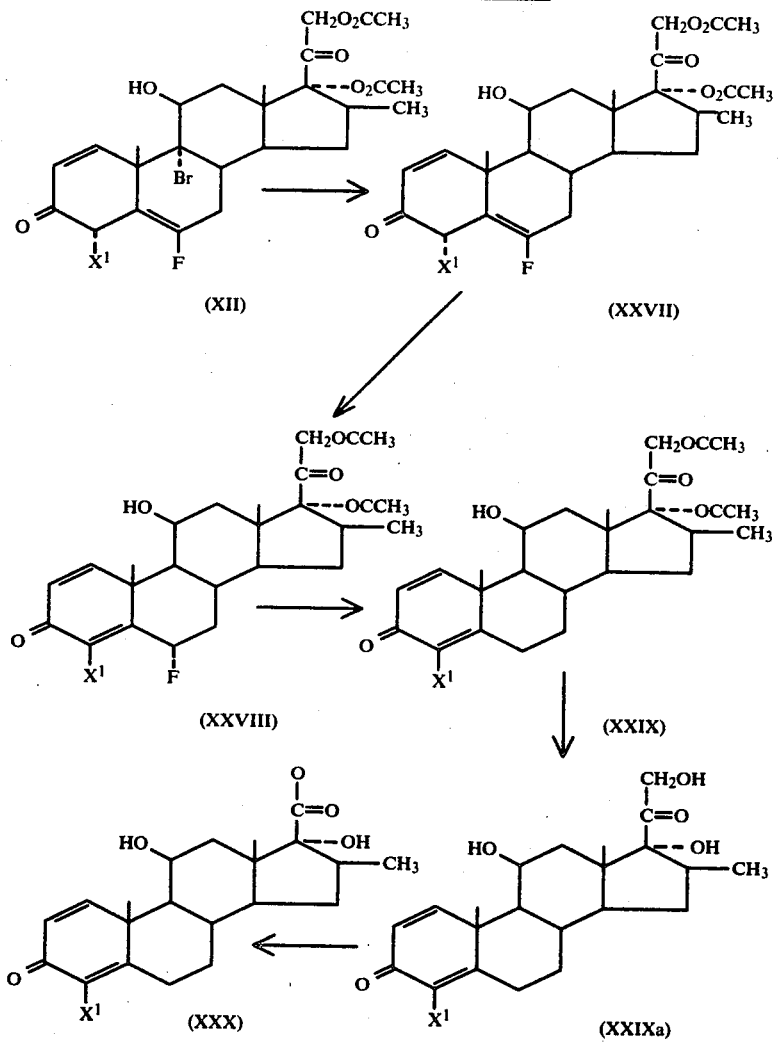

In this process, the starting compound of Formula (XXII) (prepared as discussed in Reaction Sequence 1) is treated with a molar excess (preferably 10-15 times) of tributyl tin hydride in tetrahydrofuran at reflux temperature until the reaction is complete, generally about 2-3 hours. This results in a compound having a hydrogen at the 9α-position represented by Formula (XXXVII). This in turn is converted to a compound of Formula (XXVIII) by treatment with potassium fluoride as discussed hereinbefore. This is then converted to the compound represented by Formula (XXIX) is zinc metal dust, cupric acetate, acetic acid in metanol and methylene chloride using methods discussed hereinbefore. This is converted to the etianic acid derivative as discussed before.

In Reaction Sequence 5, below, compounds of this invention are prepared which are unsubstituted at both the 6α and 9α positions.

REACTION SEQUENCE 5

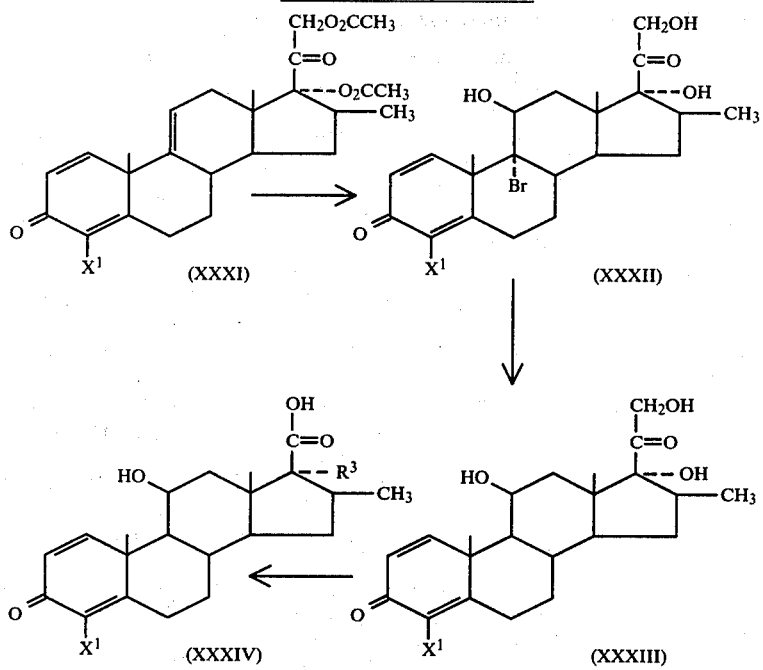

The compound represented by Formula (XXXI) is known. The 9,11-bromohydrin of Formula (XXII) is prepared using dibromohydantoin according to methods known in the art and then is converted to the 9-desbromo compound of Formula (XXXIII) using tributyl tin hydride as discussed hereinabove. That compound is then converted to a compound represented by Formula (XXXIV) wherein $X^1$ is defined hereinbefore.

More specific embodiments of the process of this invention are given hereafter in the Examples.

Administration and Formulation

The compounds of this invention are useful for the relief of inflamed conditions in mammals, and more specifically are useful for relieving inflammatory manifestations of corticosteroid responsive dermatoses. Initial approximation of anti-inflammatory activity is done by following the procedure of McKenzie, S. W. and Stoughton, R. B., "Method for Comparing Percutaneous Absorption of Steroids" Arch Dermat, 86, 608 (1962) or modifications thereof.

Generally, the inflammatory manifestation in mammals, particularly humans, is combatted by treating the afflicted mammal with a therapeutically effective amount of the novel steroids of this invention, that is an amount which results in improvement of the inflamed condition. Preferably the steroids are first formulated to prepare a suitable pharmaceutical formulation, as discussed hereinafter, which is then placed in contact with the afflicted area. An effective amount will depend upon the particular condition and the mammal receiving the treatment but will vary between 0.001% to 10% by weight of the pharmaceutical composition and preferably will be between 0.01 and 1% by weight of the formulation. Using these levels in the formulation, a therapeutically effective, non-side effect producing amount, i.e. enough to effect an anti-inflammatory response, but not enough to adversely effect the recipient, is applied to the inflamed area.

The compounds of this invention not only have anti-inflammatory activity but also exhibit a low level of systemic activity, as measured by recognized laboratory assays. This allows for the application of an effective amount of the anti-inflammatory compounds with little adverse effect on the rest of the mammal's system.

The novel steroids of this invention may be formulated with suitable pharmaceutical excipients known in the art to form particularly effective anti-inflammatory compositions. Generally an effective amount of the steroid is about 0.001% w to about 10%w of the total formulated composition. The rest of the formulated composition will be about 90%w to about 99.999%w of at least one suitable excipient which may include a pharmaceutically acceptable solvent and other pharmaceutically acceptable additives to form an effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, suppositories, aerosols, solutions or the like. Particularly suitable solvents include water, glycerine, propylene carbonate, and a glycol such as 1,2-propylene diol (i.e. propylene glycol), 1,3-propylene diol, polyethylene glycol having a molecular weight of from 100 to 10,000, dipropylene glycol etc.; and mixtures of the aforementioned with each other.

A topical cream may be prepared as a semi-solid emulsion of oil in water or water in oil. A cream base formulation by definition is an emulsion which is a two-phase system with one liquid (for example fats or oils) being dispersed as small globules in another substance (e.g., a glycol-water solvent phase) which may be employed as the primary solvent for the novel steroids therein, the cream formulation may contain fatty alcohols, surfactants, mineral oil or petrolatum and other typical pharmaceutical adjuvants such as anti-oxidants, antiseptics, or compatible adjuvants. A typical cream base formulation is given in the following table:

| | |
|---|---|
| Water/glycol mixture (15% or more glycol) | 50–99 parts by weight |
| Fatty alcohol | 1–20 |
| Non-ionic Surfactant | 0–10 |
| Mineral oil | 0–10 |
| Typical pharmaceutical adjuvants | 0–5 |
| Active Ingredients | 0.001–10 |

The fatty alcohol, non-ionic surfactant, and other adjuvants are discussed in U.S. Pat. No. 3,934,013 to Poulsen which is incorporated herein by reference.

The novel steroids of this invention may also be formulated as ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | |
|---|---|
| White petrolatum | 40–94 parts by weight |
| Mineral Oil | 5–20 |
| Glycol solvent | 1–15 |
| Surfactant | 0–10 |
| Stabilizer | 0–10 |
| Active Ingredients | 0.001–10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much as those applications as is pertinent is incorporated herein by reference. Following is a typical ointment base formulation containing propylene carbonate:

| | |
|---|---|
| Active Ingredients | 0.001–10.0 parts by weight |
| Propylene Carbonate | 1–10 |
| Solvent | 1–10 |
| Surfactant | 1–10 |
| White Petrolatum | 70–97 |

Suitable solvents, surfactants, stabilizers, etc. are discussed in U.S. Pat. No. 3,934,013 and such discussion is incorporated herein by reference.

A suitable "non-classical" anhydrous, water washable "ointment type" base is described in U.S. Pat. No. 3,952,930 to Katz and Neiman, and that patent is incorporated herein by reference. A representative composition of this invention utilizing such a base is as follows:

| | |
|---|---|
| Glycol solvent | 40–35 parts by weight |
| Fatty alcohol | 15–45 |
| Compatible plasticizer | 0–15 |
| Compatible coupling Agent | 0–15 |
| Penetrant | 0–20 |
| Active Ingredients | 0.001–10.0 |

PREPARATION 1

4α,6-Difluoro-9α-bromo-11β-hydroxy-16β-methyl-17α,21-diacetoxypregna-1,5(6)-diene-3,20-dione A mixture of 5.0 g of 6α-fluoro-16β-methyl-17α,21-diacetoxypregna-4,9(11)-diene-3,20-dione (prepared according to British Pat. No. 1,403,962), 100 ml of dioxane and 3.5 g of 2,3-dichloro-4,6-dicyano-1,4-benzoquinone is refluxed for 10 hours. The mixture is then cooled, filtered and evaporated to dryness. The residue is dissolved in acetone and this solution is then filtered through 100 g of alumina and concentrated to yield 6α-fluoro-16β-methyl-17α,21-diacetoxypregna-1,4,9(11)-triene-3,20-dione which is further purified by recrystallization from acetone:hexane.

Ten (10) g of 6α-fluoro-16β-methyl-17α,21-diacetoxypregna-1,4,9(11)-triene-3,20-dione in 110 ml of dioxane (A.R.) plus 2.2 mls of a solution of 4.4 ml 70% $HClO_4$ in 200 mls of water, is treated with 4 g of dibromohydantoin in the dark at R.T. for a period of one hour or when TLC using 50% ethyl acetate/50% hexane shows the reaction to be complete. The reaction mixture is precipitated in 2 l of water, stirred for 10 minutes and the crystalline precipitate collected by filtration, washed with water, and air dried to give 11.4 g of 6α-fluoro-9α-bromo-11β-hydroxy-16β-methyl-17α,21-diacetoxypregna-1,4-diene-3,20-dione.

The bromohydrin prepared in this manner (19.1 g) is mixed with 286 ml of methyl orthoformate, 96 ml of anhydrous methanol and 1.9 ml of fuming sulfuric acid and heated on a water bath at 50°–55° C. for 15 minutes. The mixture is treated with 15 ml of pyridine and poured into 300 ml of water, separated and washed three times with water. The resulting mixture is dried over anhydrous sodium sulfate, filtered and concentrated under high vacuum to a foam which is left in crushed dry ice for 16 hours to give the 11β-orthoester of 3-methoxy-6α-fluoro-9α-bromo-16β-methyl-17α,21-diacetoxypregna-1,3,5(6)-triene-20-one. The orthoester so obtained is dissolved in 300 ml of a mixture of 80% THF/20% water and treated at room temperature with a slow stream of $ClO_3F$ until no more starting material is detected by TLC analysis. The mixture is diluted with water and the organic solvent eliminated under reduced pressure (high vacuum) at 50°–55° C. The mixture is diluted with water up to 2 liters and kept in the refrigerator for 20 hours. The resulting precipitate is filtered and dried. One (1) g of crude reaction mixture is dissolved in about 20 ml of methylene dichloride (MDC) and filtered through a 10 g column of silica with 100% MDC. The column is eluted with 1.2 liters of MDC, then with 2% ethyl acetate/98% MDC. The homgeneous fractions (containing small amounts of negative and positive polar impurities) are concentrated to dryness under high vacuum. NMR analysis of the negative polar product eluted indicates that the product is 4α,6-difluoro-9α-bromo-11β-hydroxy-16β-methyl-17α,21-diacetoxypregna-1,5(6)-diene-3,20-dione.

PREPARATION 2

4-fluoro-9,11-expoxy-16β-methyl-17α,21-hydroxypregna-1,4-diene-3,20-dione-21-acetate.

The resulting 9,11-bromohydrin from Preparation 1 of this example is stirred with methanol containing anhydrous potassium carbonate under nitrogen until TLC shows the reaction is complete. The reaction mixture is diluted with methanol and glacial acetic acid and concentrated under reduced pressure to a small volume. The precipitate is collected by filtration and washed with methanol and water to give a product containing 4,6α-difluoro-9,11-epoxy-16β-methyl-17α,21-dihydroxypregna-1,4-diene-3,20-dione which in turn is reacted with acetic anhydride in pyridine at room temperature for 15 hours (or until TLC shows the reaction is complete). The mixture is then poured into ice water and the solid which forms is collected by filtration, washed with water and dried to yield a product containing 4,6α-difluoro-9,11-expoxy-16β-methyl-17α,21-dihydroxypregna-1,4-diene-3,20-dione 21-acetate which is further purified through recrystallization from acetone:hexane or high pressure liquid chromatography.

Six hundred (600) mg of zinc metal dust containing 3% cupric acetate (previously blended with mortar and pestle) and 100 ml of a 1:1 mixture of dry methanol and methylene chloride are stirred together in a heat-dried nitrogen blanketed 500 ml three neck flask with septum, addition funnel, and magnetic stirrer. A solution of 2.0 g of the product containing 4,6α-difluoro-9,11-epoxy-16β-methyl-17α,21-dihydroxy-21-acetate in 120 ml of 1:1 methanol-methylene chloride solvent mixture is placed in the addition funnel and 0.6 ml of glacial acetic acid is added to the zinc slurry via syringe and stirred together for 20 minutes, after which all of the solution of the oxide is added from the addition funnel.

After 2½ hours, the reaction mixture is cooled in ice, then filtered through a cake of celite, washing thrice with the methanol-methylene chloride solvent mixture. The pH of the filtrate is adjusted to pH 7 with a solution of 1.5% potassium carbonate in methanol containing 10% water (the transient pregna-1,5-diene spontaneously rearranges to pregna-1,4-diene in neutral solution) and the methanol and methylene chloride are then evaporated while ethyl acetate is added to replace them. The ethyl acetate solution is washed three times with water, then dried over sodium sulfate and subsequently is stripped to dryness.

The residue is applied to a silica gel column prepared in 1% methanol-methylene chloride and is developed by gradient elution up to 4% methanol-methylene chloride. Recovery of material from the appropriate fractions and recrystallization from acetone-hexane affords 502 mg of 98+% pure 4-fluoro-9,11-epoxy-16β-methyl-17α,21-dihydroxypregna-1,4-diene-3,20-dione 21-acetate.

PREPARATION 3

4,6α-Difluoro-11β,17α,21-trihydroxy-16β-methylpregna-1,4-diene-3,20-dione

The resulting product from Preparation 1 of this Example is mixed with a tenfold molar excess of tributyl tin hydride in tetrahydrofuran in a nitrogen atmosphere at reflux for two hours to eliminate the 9α-bromine and form 4α,6-difluoro-11β-hydroxy-16β-methyl-17α,21-diacetoxypregna-1,5(6)-diene-3,20-dione.

The resulting product is stirred with a molar excess of potassium fluoride in dimethyl sulfoxide (DMSO) at 60°-65° C. until t.l.c. indicates the reaction complete and 4,6α-difluoro-11β-hydroxy-16β-methyl-17α,21-diacetoxypregna-1,4-diene-3,20-dione is formed.

This product, in turn, is stirred with methanol containing anhydrous potassium carbonate under nitrogen at atmospheric pressure and ambient temperature until TLC shows the reaction is complete. The reaction mixture is diluted with methanol and glacial acetic acid and concentrated under reduced pressure to a small volume. The crystalline precipitate which forms is collected by filtration and washed with methanol and water to give 4,6α-difluoro-11β,17α,21-trihydroxy-16β-methylpregna-1,4-diene-3,20-dione.

PREPARATION 4

4,6α,9α-Trifluoro-11β-17α,21-trihydroxy-16β-methylpregna-1,4-diene-3,20-dione.

To a stirred solution of 1.8 g of 4,6α-difluoro-9,11-epoxy-16β-methyl-17α,21-dihydroxypregna-1,4-diene-3,20-dione (from Preparation 2, second paragraph) in 30 ml of methylene chloride, cooled to 0° C. is added a cooled (−70° C.) of 2.11 g of anhydrous hydrogen fluoride in 3.7 ml of tetrahydrofuran over a period of 20 minutes. The mixture is stirred at a temperature below 10° C. for six hours and then neutralized by cautious addition of a 5% aqueous sodium bicarbonate solution. The organic layer is separated, washed with water, dried over sodium sulfate and concentrated until solid forms. The cooled mixture is then filtered and the solid dissolved in hot ethyl acetate. This solution is filtered hot and then cooled and the solid which forms is collected by filtration to yield 4,6α,9α-trifluoro-11β,17α,21-trihydroxy-16β-methylpregna-1,4-diene-3,20-dione.

PREPARATION 5

4,9α-difluoro-11β,17α,21-trihydroxy-16β-methylpregna-1,4-diene-3,20-dione.

4-Fluoro-9,11-epoxy-16β-methyl-17α,21-dihydroxypregna-1,4-diene-3,20-dione 21-acetate (from Preparation 2) is reacted with anhydrous hydrogen fluoride according to the procedure of Preparation 4 to give 4,9α-difluoro-11β,17α,21-trihydroxy-16β-methylpregna-1,4-diene-3,20-dione 21-acetate. This compound in turn is treated with a small amount methanol containing anhydrous potassium carbonate under nitrogen at atmospheric pressure and ambient temperature until TLC shows that the hydrolysis of the ester is complete. The reaction mixture is diluted with methanol and glacial acetic acid and concentrated under reduced pressure to a small volume. The crystalline precipitate which forms is collected by filtration and washed with methanol and water to give 4,9α-difluoro-11β,17α,21-trihydroxy-16β-methylpregna-1,4-diene-3,20-dione.

PREPARATION 6

4α-Chloro-6-fluoro-9α-bromo-11β-hydroxy-16β-hydroxy-16β-methyl-17α,21-diacetoxypregna-1,4(6)-diene-3,20-dione.

By following in principle the procedure of Preparation 1 but substituting N-chlorosuccinimide for perchloryl fluoride (ClO₃F) one obtains 4α-chloro-6-fluoro-9α-bromo-11β-hydroxy-16β-hydroxy-16β-methyl-17α,21-diacetoxypregna-1,4(6)-diene-3,20-dione.

PREPARATION 7

4-Chloro-9,11-epoxy-16β-methyl-17α,21-dihydroxypregna-1,4-diene-3,20-dione-21-acetate.

By following in principle the procedure of Preparation 2 but substituting 4α-chloro-6-fluoro-9α-bromo-11β-hydroxy-16α-methyl-17α,21-diacetoxypregna-1,4(6)-diene-3,20-dione for the corresponding 4α-fluoro compound, one obtains 4-chloro-9,11-epoxy-16β-methyl-17α,21-dihydroxy-pregna-1,4-diene-3,20-dione-21-acetate.

PREPARATION 8

4-Chloro-6α-fluoro-11β,17α,21-trihydroxy-16β-methylpregna-1,4-diene-3,20-dione.

By following in principle the procedure of Preparation 3 but substituting 4α-chloro-6-fluoro-9α-bromo11β-hydroxy-16β-methyl-17α,21-diacetoxypregna-1,5(6)-diene-3,20-dione for the corresponding 4α-fluoro compound, one obtains 4-chloro-6α-fluoro-11β,17α,21-trihydroxy-16β-methylpregna-1,4-diene-3,20-dione.

PREPARATION 9

4-Chloro-6α,9α-difluoro-11β,17α,21-trihydroxy-16β-methylpregna-1,4-diene-3,20-dione.

By following in principle the procedure of Preparation 4 by substituting 4-chloro-6α-fluoro-9,11-epoxy-16β-methyl-17α,21-dihydroxypregna-1,4-diene-3,20-dione for the corresponding 4-fluoro compound, one obtains 4-chloro-6α,9α-difluoro-11β,17α,21-trihydroxy-16β-methylpregna-1,4-diene-3,20-dione.

PREPARATION 10

4-Chloro-9α-fluoro-11β,17α,21-trihydroxy-16β-methylpregna-1,4-diene-3,20-dione.

By following in principle the procedure of Preparation 5 but substituting 4-chloro-9,11-epoxy-16β-methyl-17α,21-dihydroxypregna-1,4-diene-3,20-dione for the corresponding 4-fluoro compound, one obtains 4-chloro-9α-fluoro-11β,17α,21-trihydroxy-16β-methylpregna-1,4-diene-3,20-dione.

PREPARATION 11

A. One gram of 4,6α-difluoro-11β,17α,21-trihydroxy-16β-methylpregna-1,4-diene-3,20-dione is stirred in a mixture of periodic acid, methanol and water at room temperature until t.l.c. indicates that the reaction is complete. The organic product is extracted with ethyl acetate three times and the organic phases are combined, washed with water, dried over sodium sulfate and evaporated. The residue is recrystallized from a suitable solvent to give 3-oxo-4,6α-difluoro-11β,17α-dihydroxy-16β-methylandrosta-1,4-diene 17β-carboxylic acid.

B. Similarly, by following in principle the procedure of Part A of this example, but substituting the compounds prepared in Preparations 4, 5 and 8–10 for 4,6α-difluoro-11β,17α,21-trihydroxy-16β-methylpregna-1,4-diene-3,20-dione, one obtains 3-oxo-4,6α,9α-trifluoro-11β,17α-dihydroxy-16β-methylandrosta-1,4-diene 17β-carboxylic acid;
3-oxo-4,9α-difluoro-11β,17α-dihydroxy-16β-methylandrosta-1,4-diene 17β-carboxylic acid;
3-oxo-4-chloro-6α-fluoro-11β,17α-dihydroxy-16β-methylandrosta-1,4-diene 17β-carboxylic acid;
3-oxo-4-chloro-6α,9α-difluoro-11β,17α-dihydroxy-16β-methylandrosta-1,4-diene 17β-carboxylic acid; and
3-oxo-4-chloro-9α-fluoro-11β,17α-dihydroxy-16β-methylandrosta-1,4-diene 17β-carboxylic acid.

PREPARATION 12

A. One (1.0) g of 3-oxo-4,6α-difluoro-11β,17α-dihydroxy-16β-methylandrosta-1,4-diene 17β-carboxylic acid is treated at room temperature with 50 ml of propionic anhydride and 5.0 ml of anhydrous pyridine. The mixture is stirred for one hour, then slowly diluted with water up to 200 liters while the mixture is cooled in an ice-water bath. The crystalline precipitate so obtained is collected by filtration, washed with water and dried, to give 3-oxo-4,6α-difluoro-11β-hydroxy-16β-methyl-17α-propionyloxyandrosta-1,4-diene 17β-carboxylic acid.

B. Similarly, by substituting other compounds prepared as in Preparation 11 for 3-oxo-4,6α-difluoro-11β,17α-dihydroxy-16β-methylandrosta-1,4-diene 17-carboxylic acid, other compounds of this invention are obtained such as 3-oxo-4,6α,9α-trifluoro-11β-hydroxy-16β-methyl-17α-propionyloxyandrosta-1,4-diene 17β-carboxylic acid;
3-oxo-4,9α-difluoro-11β-hydroxy-16β-methyl-17α-propionyloxyandrosta-1,4-diene 17β-carboxylic acid;
3-oxo-4-chloro-6α-fluoro-11β-hydroxy-16β-methyl-17α-propionyloxyandrosta-1,4-diene 17β-carboxylic acid;
3-oxo-4-chloro-6α,9α-difluoro-11β-hydroxy-16β-methyl-17α-propionyloxyandrosta-1,4-diene 17β-carboxylic acid;
3-oxo-4-chloro-9α-fluoro-11β-hydroxy-16β-methyl-17α-propionyloxyandrosta-1,4-diene 17β-carboxylic acid;

C. By substituting acetic anhydride, n-butyric anhydride, valeric anhydride, or caproic anhydride for propionic anhydride, the corresponding 17α-acetates, -n-butyrates, valerates or caproates are prepared, e.g.

3-oxo-4,6α-difluoro-11β-hydroxy-16β-methyl-17α-acetoxyandrosta-1,4-diene 17β-carboxylic acid;
3-oxo-4,6α,9α-trifluoro-11β-hydroxy-16β-methyl-17α-butyroxyandrosta-1,4-diene 17β-carboxylic acid;
3-oxo-4,6α-difluoro-11β-hydroxy-16β-methyl-17α-valeryloxyandrosta-1,4-diene 17β-carboxylic acid;
3-oxo-4,6α,9α-trifluoro-11β-hydroxy-16β-methyl-17α-caproyloxyandrosta-1,4-diene 17β-carboxylic acid;
and the like.

EXAMPLE 1

A. In a heat-dried, stirred, $N_2$ blanketed 25 ml flask with side-arm and septum 130 mg of 3-oxo-4,6α-difluoro-11β,hydroxy-16β-methyl-17α-propionyloxyandrosta-1,4-diene-17β-carboxylic acid is dissolved in 8 ml of dry THF. Fifty-nine (59) μl of triethylamine followed by 81 μl of diphenyl chlorophosphate are added, and the turbid mixture is heated in a 55° oil bath. After 2 hours the reaction mixture is cooled in ice and then filtered into a fresh, dry $N_2$ blanketed 50 ml flask with side-arm and septum, washing filter cake with additional THF.

1.35 Ml of a 0.92 N solution of sodium thiomethylate (sodium methyl mercaptan) is added to the solution of the intermediate in the flask, and the mixture is heated at 55° for 1½ hours, after which the reaction is complete. The resulting product is dumped into ethyl acetate and dilute aqueous sodium bicarbonate is added. The extract is washed three times with $H_2O$, dried over $Na_2SO_4$, and evaporated to dryness. Two crystallizations of the residue from acetone-hexane affords 67 mg of 98% pure colorless needles of methyl 3-oxo-4,6α-difluoro-11β-hydroxy-16β-methyl-17α-propionyloxyandrosta-1,4-diene 17β-thiocarboxylate.

B. Similarly, by following in principle the procedures of Part A of this Example but substituting the compounds named in Part B of Preparation 12 for 3-oxo-4,6α-difluoro-11β-hydroxy-16β-methyl-17α-propionyloxyandrosta-1,4-diene 17β-carboxylic acid, other compounds of this invention are obtained such as
methyl-3-oxo-4,6α,9α-trifluoro-11β-hydroxy-16β-methyl-17α-propionyloxyandrosta-1,4-diene 17β-thiocarboxylate;
methyl-3-oxo-4,9α-difluoro-11β-hydroxy-16β-methyl-17α-propionyloxyandrosta-1,4-diene 17β-thiocarboxylate;
methyl-3-oxo-4-chloro-6α-fluoro-11β-hydroxy-16β-methyl-17α-propionyloxyandrosta-1,4-diene 17β-thiocarboxylate;
methyl-3-oxo-4-chloro-6α,9α-difluoro-11β-hydroxy-16β-methyl-17α-propionyloxyandrosta-1,4-diene 17β-thiocarboxylate;
methyl-3-oxo-4-chloro-9α-fluoro-11β-hydroxy-16β-methyl-17α-propionyloxyandrosta-1,4-diene 17β-thiocarboxylate.

C. Similarly, by following in principle the procedures of Part A of this Example but substituting the compounds named in Part C of Preparation 12 for 3-oxo-4,6α-difluoro-11β-hydroxy-16β-methyl-17α-propionyloxyandrosta-1,4-diene 17β-carboxylic acid, other compounds of this invention are obtained such as
methyl-3-oxo-4,9α-difluoro-11β-hydroxy-16β-methyl-17α-acetoxy-androsta-1,4-diene 17β-thiocarboxylate;
methyl-3-oxo-4,9α-difluoro-11β-hydroxy-16β-methyl-17α-butyroxyandrosta-1,4-diene 17β-thiocarboxylate;
methyl-3-oxo-4,9α-difluoro-11β-hydroxy-16β-methyl-17α-valeryloxyandrosta-1,4-diene 17β-thiocarboxylate;
methyl-3-oxo-4,9α-difluoro-11β-hydroxy-16β-methyl-17α-caproyloxyandrosta-1,4-diene 17β-thiocarboxylate; and the like.

EXAMPLE 2

A. By following in principle the procedure of Example 1, Part A but substituting sodium thioethylate, sodium thiopropylate, sodium thiobutylate or sodium thiohexylate for sodium thiomethylate, other compounds of this invention are obtained such as
ethyl 3-oxo-4,6α-difluoro-11β-hydroxy-16β-methyl-17α-propionyloxyandrosta-1,4-diene 17β-thiocarboxylate;
propyl 3-oxo-4,6α-difluoro-11β-hydroxy-16β-methyl-17α-propionyloxyandrosta-1,4-diene 17β-thiocarboxylate;
butyl 3-oxo-4,6α-difluoro-11β-hydroxy-16β-methyl-17α-propionyloxyandrosta-1,4-diene 17β-thiocarboxylate.
hexyl 3-oxo-4,6α-difluoro-11β-hydroxy-16β-methyl-17α-propionyloxyandrosta-1,4-diene 17β-thiocarboxylate.

B. In a similar manner, by following the procedure of Part A of this example but employing the compounds of Preparation 12, Part B for 3-oxo-4,6α-difluoro-11β-hydroxy-16β-methyl-17α-propionyloxyandrosta-1,4-diene 17β-carboxylic acid, other compounds of this invention are prepared such as
ethyl-3-oxo-4,6α,9α-trifluoro-11β-hydroxy-16β-methyl-17α-propionyloxyandrosta-1,4-diene 17β-thiocarboxylate;
ethyl-3-oxo-4,9α-difluoro-11β-hydroxy-16β-methyl-17α-propionyloxyandrosta-1,4-diene 17β-thiocarboxylate;
ethyl-3-oxo-4-chloro-6α-fluoro-11β-hydroxy-16β-methyl-17α-propionyloxyandrosta-1,4-diene 17β-thiocarboxylate;
ethyl-3-oxo-4-chloro-6α,9α-difluoro-11β-hydroxy-16β-methyl-17α-propionyloxyandrosta-1,4-diene 17β-thiocarboxylate;
ethyl-3-oxo-4-chloro-9α-fluoro-11β-hydroxy-16β-methyl-17α-propionyloxyandrosta-1,4-diene 17β-thiocarboxylate.

C. In a similar manner, by following the procedure of Part A of this example but employing the compounds of Preparation 12, Part C for 3-oxo-4,6α-difluoro-11β-hydroxy-16β-methyl-17α-propionyloxyandrosta-1,4-diene 17β-carboxylic acid, other compounds of this invention are prepared such as
ethyl-3-oxo-4,6α,9α-trifluoro-11β-hydroxy-16β-methyl-17α-acetoxyandrosta-1,4-diene 17β-thiocarboxylate;
ethyl-3-oxo-4,9α-difluoro-11β-hydroxy-16β-methyl-17α-butyroxyandrosta-1,4-diene 17β-thiocarboxylate;
ethyl-3-oxo-4,6α-difluoro-11β-hydroxy-16β-methyl-17α-valeryloxyandrosta-1,4-diene 17β-thiocarboxylate;
ethyl-3-oxo-4,6α,9α-trifluoro-11β-hydroxy-16β-methyl-17α-caproyloxyandrosta-1,4-diene 17β-thiocarboxylate; and the corresponding propyl, butyl and hexyl esters.

EXAMPLE 3

This example sets forth a process for hydrogenating the androsta-1,4-dienes to androst-4-enes of this invention.

A solution of 25 mg of tris-(triphenylphosphine)-chlororhodium in 6 ml of benzene and 15 ml of ethanol is stirred under hydrogen for 60 minutes. 4,6α,9α-Trifluoro-11β,17α-dihydroxy-16β-methyl-3-oxoandrosta-1,4-diene-17β-thiocarboxylic acid (250 mg) is added and the resulting solution is stirred under hydrogen at room temperature at atmospheric pressure. After hydrogen uptake is complete, the solution is evaporated to dryness and the residue taken up in a mixture of petroleum ether and methylene chloride. The pure product is isolated by column chromatography on silica gel to give 4,6α,9α-trifluoro-11β,17α-dihydroxy-16β-methylandrost-4-ene-17β-thiocarboxylic acid.

Similarly, by substituting other androsta-1,4-dienes of this invention, other corresponding androst-4-enes are prepared such as n-hexyl 17α-acetoxy-4-chloro-6α-fluoro-11β-hydroxy 16β-methyl-3-oxoandrosta-4-ene 17β-thiocarboxylate, and the like.

EXAMPLE 4

This example sets forth a process for preparing an 11-keto compound of this invention by oxidizing any of the 11β-hydroxy steroids set forth in Preparations I–VI.

One g of 4,6α,9α-trifluoro-11β-hydroxy-16β-methyl-3-oxo-17α-propionyloxyandrost-1,4-diene 17β carboxylic acid is dissolved in 50 ml of acetone and treated at room temperature with Jone's reagent (chromic anhydride in dilute sulfuric acid) dropwise until TLC indicates the absence of starting material. The mixture is treated with five drops of isopropyl alcohol to destroy any excess of reagent, then diluted with 50 ml of water and the mixture concentrated under vacuum under reduced pressure to give a crystalline material, namely 4,6α,9α-trifluoro-16β-methyl-3,11-dioxo-17α-propionyloxyandrost-1,4-diene 17β-carboxylic acid.

The resulting compound is then reacted according to procedures of Examples 1–2 to obtain an 11-keto steroid of this invention.

EXAMPLE 5

A mixture of 0.5 g of methyl 3-oxo-4,6α-difluoro-11β-hydroxy-16β-methyl-17α-propionyloxyandrost-4-ene 17β-thiocarboxylate, 10 ml of dioxane and 0.35 g of 2,3-dichloro-5,6-dicyano-1,4-benzoquinone is refluxed for 10 hours. The mixture is then cooled, filtered and evaporated to dryness. The residue is dissolved in acetone and this solution is then filtered through 10 g of alumina and concentrated to yield methyl 4,6α-difluoro-11β-hydroxy-16β-methyl-3-oxo-17α-propionyloxyandrosta-1,4-diene 17β-thiocarboxylate, which is further purified by recrystallization from acetone:hexane.

Other androsta-1,4-diene 17β-carboxylates of this invention are prepared by following in principle the above procedure but substituting other appropriate androst-4-ene 17β thiocarboxylates for the above-named starting material.

EXAMPLE 6—Formulation

In this example a formulation is prepared of the following composition

|  | % w/w |
|---|---|
| Methyl 4,6α,9α-trifluoro-11β-hydroxy-16β-methyl-3-oxo-17α-propionyloxyandrosta-1,4-diene 17β-thiocarboxylate | 0.025 |
| Stearyl Alcohol | 30.0 |
| PEG 6000 | 5.0 |
| 1,2,6-Haxanetriol | 2.5 |
| Citric Acid Anhydrous, USP | 0.02 |
| Propylene Glycol, USP, q.s. | 100.0 |

The steroid is dissolved in 624.8 grams of propylene glycol at 90°–95° C. The latter is then mixed with the other ingredients at 80°–85° C. to give the desired formulation.

EXAMPLE 7

This example sets forth an alternative method for preparing the 16β-methyl steroids of this invention.

A. Ten (10) g of 6α-fluoro-16β-methyl-17α,21-diacetoxypregna-1,4,9(11)-triene-3,20-dione in 110 mls of dioxane (A.R.) plus 2.2 mls of a solution of 4.4 mls 70% HClO₄ in 200 mls of water is treated with 4 g of dibromantoin in the dark at room temperature for one hour when TLC in 50% ethyl acetate/50% Hexane shows the reaction to be complete. The reaction mixture is diluted with 2 liters of water, stirred for 10 minutes and the crystalline precipitate collected by filtration, washed with water, and air dried to give 11.4 g of 6α-fluoro-9α-bromo-11β-hydroxy-16β-methyl-17α,21-diacetoxypregna 1,4-diene-3,20-dione.

This bromohydrin (19.1 g) is mixed with 286 ml of methyl orthoformate, 96 ml of anhydrous methanol and 1.9 ml of fuming sulfuric acid and heated on a water bath at 80°–85° for 15 minutes. The mixture is treated with 15 ml of pyridine and poured into 300 ml of water, separated and washed three times with water, dried over anhydrous sodium sulfate, filtered and concentrated under high vacuum to a foam which is cooled in crushed dry ice for 16 hours to give the 11β-orthoester of 3-methoxy-6α-fluoro-9α-bromo-16β-methyl-17α,21-diacetoxypregna-1,3,5(6)-triene-20-one.

The orthoester so obtained is dissolved in 300 ml of a mixture of 80% THF/20% water and treated at room temperature with a slow stream of perchloryl fluoride until no more starting material was detected by TLC analysis. The mixture is diluted with water and the organic solvent eliminated under reduced pressure (high vacuum) at 80°–85° C. The mixture is diluted with water up to two l and kept in the refrigerator for 20 hours. The resulting precipitate is filtered and air dried.

One (1) g of crude reaction mixture is dissolved in about 20 mls of methylene dichloride (MDC) and filtered through a 10 g column of silica with 100% MDC. The column was eluted with 1.2 liters of MDC, then with a mixture of 2% ethyl acetate/98% MDC. The homogeneous fractions containing small amounts of negative and positive polar impurities are concentrated to dryness under a high vacuum. NMR analysis of the negative polar product eluted indicates that the product is 4,6α-difluoro-9α-bromo-11β-hydroxy-16β-methyl-17α,21-diacetoxypregna-1,5(6)-diene-3,20-dione.

The resulting product is mixed with tin tributylhydride in tetrahydrofuran at room temperature to eliminate the 9α-bromine and form 4,6α-difluoro-11β-hydroxy-16β-methyl-17α,21-diacetoxypregna-1,5(6)-3,20-dione (The reaction may be accelerated by adding a small amount of a free radical and refluxing).

The resulting product is stirred with methanol containing anhydrous potassium carbonate under nitrogen at atmospheric pressure and ambient temperature until TLC shows the reaction is complete. The reaction mixture is diluted with methanol and glacial acetic acid and concentrated under reduced pressure to a small volume. The crystalline precipitate which forms is collected by filtration and washed with methanol and water to give 4,6α-difluoro-11β-hydroxy-16β-methyl-17α,21-dihyroxypregna-1,4-diene-3,20-dione.

The resulting product is reacted with aqueous periodic acid ($H_5IO_6$) in methanol at room temperature until the reaction is complete as judged by TLC. The methanol is removed by evaporation, water is added and the resulting precipitate removed by filtration and purified by crystallization to give 4,6α-difluoro-11β,17α-dihydroxy-16β-methyl-3-oxoandrosta-1,4-diene 17β-carboxylic acid.

This product is then reacted with propionic anhydride and pyridine according to the process set forth in Preparation I, Part A to give the corresponding 17α-propionyloxy derivative which, in turn, is reacted in principle according to the process of Example 1, Part A to give methyl 4,6α-difluoro-11β-hydroxy-16β-methyl-3-oxo-17-propionyloxyandrosta-1,4-diene 17β-thiocarboxylate.

B. The final compound resulting from Part A of this example is further elaborated into other compounds of this invention by first forming the corresponding androsta-1,4,9(11)-triene. This is accomplished by any means known in the art such as dissolving methyl 4,6α-difluoro-11β-hydroxy-16β-methyl-3-oxo-17-propionyloxy androsta-1,4-diene 17β-thiocarboxylate in DMF, adding methylsulfonyl chloride and pyridine and heating at about 80° C. until the reaction is complete. The product is extracted with an organic solvent such as ethyl acetate, washed with water, dried over sodium sulfate and evaporated to yield methyl 4,6α-difluoro-16β-methyl-3-oxo-17α-propionyloxyandrosta-1,4,9(11)-triene 17β-thiocarboxylate. This, in turn, is chlorinated using chlorine in carbon tetrachloride according to methods known in the art to give methyl 4,6α-difluoro-9α,11β-dichloro-16β-methyl-3-oxo-17α-propionyloxyandrosta-1,4-diene 17β-thiocarboxylate.

What is claimed is:

1. A compound chosen from those represented by the formula

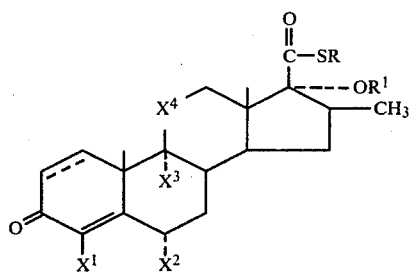

(I)

wherein
X¹ is fluoro or chloro;
X² is fluoro, chloro or hydrogen;
X³ is fluoro, chloro, bromo or hydrogen;
X⁴ is =C=O or

or may also be

when X³ is chloro;
R is alkyl of 1 through 6 carbon atoms or phenyl or benzyl optionally substituted with one substituent on the phenyl ring chosen from the group consisting of alkyl of 1 through 4 carbon atoms, alkoxy of 1 through 4 carbon atoms and halo;
R¹ is hydrogen or alkanoyl of 2 through 6 carbon atoms; and
the solid and broken lines between C-1 and C-2 represent a double or a single bond.

2. The compound of claim 1 wherein
R is alkyl of one through six carbon atoms;
R¹ is alkanoyl of two through six carbon atoms when X¹ is fluoro or chloro;
X² is fluoro or hydrogen;
X³ is fluoro, chloro or hydrogen; and
X⁴ is

or may also be

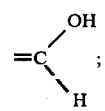

when X³ is chloro.

3. The compound of claim 2 wherein
X¹ is fluoro;
X² is hydrogen or fluoro;
X³ is hydrogen or fluoro;
X⁴ is

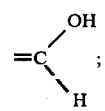

and
there is a double bond between C-1 and C-2.

4. The compound of claim 3 wherein R is methyl; R¹ is alkanoyl of 2 or 3 carbon atoms; and X¹, X² and X³ are all fluoro.

5. The compound of claim 4 wherein R¹ is alkanoyl of three carbon atoms.

6. The compound of claim 3 wherein R is methyl, R¹ is alkanoyl of 2 or 3 carbon atoms, X¹ and X² are both fluoro and X³ is hydrogen.

7. The compound of claim 6 wherein R¹ is alkanoyl of 3 carbon atoms.

8. The compound of claim 3 wherein R is methyl, R¹ is alkanoyl of 2 or 3 carbon atoms, X¹ and X³ are both fluoro and X² is hydrogen.

9. The compound of claim 8 wherein R¹ is alkanoyl of 3 carbon atoms.

10. The compound of claim 3 where R is methyl, R¹ is alkanoyl of 2 or 3 carbon atoms, X¹ is fluoro and X² and X³ are both hydrogen.

11. An anti-inflammatory pharmaceutical composition which comprises a therapeutically effective amount of the compound of claim 1 in combination with at least one suitable pharmaceutical excipient.

12. A process for treating an inflamed condition in a mammal which comprises administering a therapeutically effective amount of the compound of claim 1 to said mammal.